United States Patent [19]

Krauter et al.

[11] Patent Number: 5,575,755

[45] Date of Patent: *Nov. 19, 1996

[54] FLUID INSENSITIVE BRAKING FOR AN ENDOSCOPE

[75] Inventors: Allan I. Krauter, Syracuse; Michael Kehoskie, Jordan, both of N.Y.

[73] Assignee: Welch Allyn, Inc., Skaneateles Falls, N.Y.

[*] Notice: The term of this patent shall not extend beyond the expiration date of Pat. No. 5,464,007.

[21] Appl. No.: 388,280

[22] Filed: Feb. 13, 1995

Related U.S. Application Data

[63] Continuation-in-part of Ser. No. 200,383, Feb. 23, 1994, Pat. No. 5,464,007.
[51] Int. Cl.$^6$ .......................................................... A61B 1/00
[52] U.S. Cl. ............................................ 600/148; 600/149
[58] Field of Search ..................................... 600/146, 147, 600/148, 149, 150; 138/120; 403/358, 359, 326, 328

[56] References Cited

U.S. PATENT DOCUMENTS

| | | |
|---|---|---|
| 4,078,555 | 3/1978 | Takahashi . |
| 4,207,873 | 6/1980 | Kruy . |
| 4,461,282 | 7/1984 | Ouchi et al. . |
| 4,539,586 | 9/1985 | Danna et al. . |
| 4,617,914 | 10/1986 | Ueda . |
| 4,742,816 | 5/1988 | Suzuki et al. . |
| 4,825,850 | 5/1989 | Opie et al. . |
| 5,007,406 | 4/1991 | Takahashi et al. . |
| 5,014,685 | 5/1991 | Takahashi . |
| 5,329,887 | 7/1994 | Ailinger et al. ............................ 128/4 |
| 5,464,007 | 11/1995 | Krauter et al. .......................... 600/144 |

Primary Examiner—Richard J. Apley
Assistant Examiner—Beverly M. Flanagan
Attorney, Agent, or Firm—Harris Beach & Wilcox, LLP

[57] ABSTRACT

A fluid insensitive system for braking the displacement cables in an endoscopic insertion tube wherein at least one control wheel is mounted on the outside of the insertion tube control housing. A brake disc is mounted adjacent the control wheel and is moved in and out of engagement with the wheel by an actuator. A plurality of spring loaded detent pins are slidably carried within the control wheel for engaging a series of depressions in the brake disk to form a restraining ratchet mechanism.

23 Claims, 13 Drawing Sheets

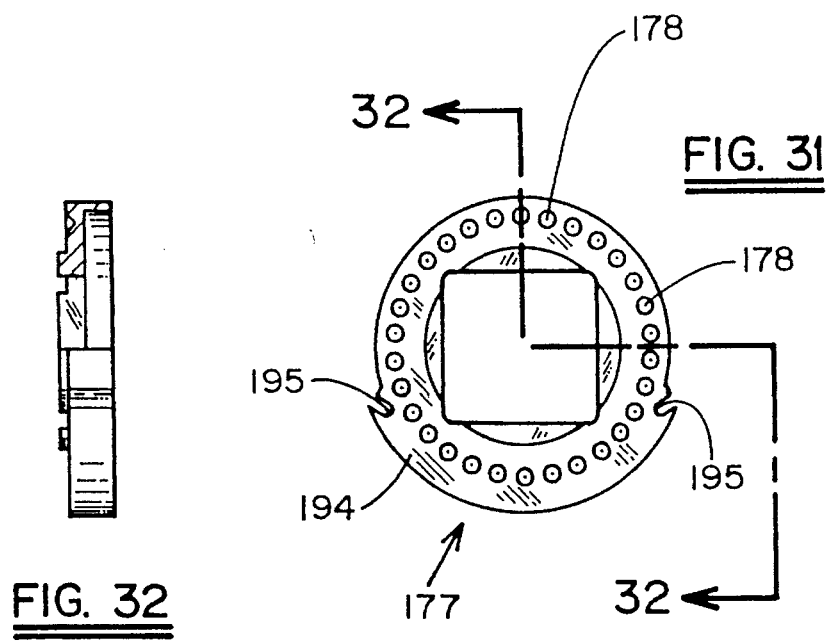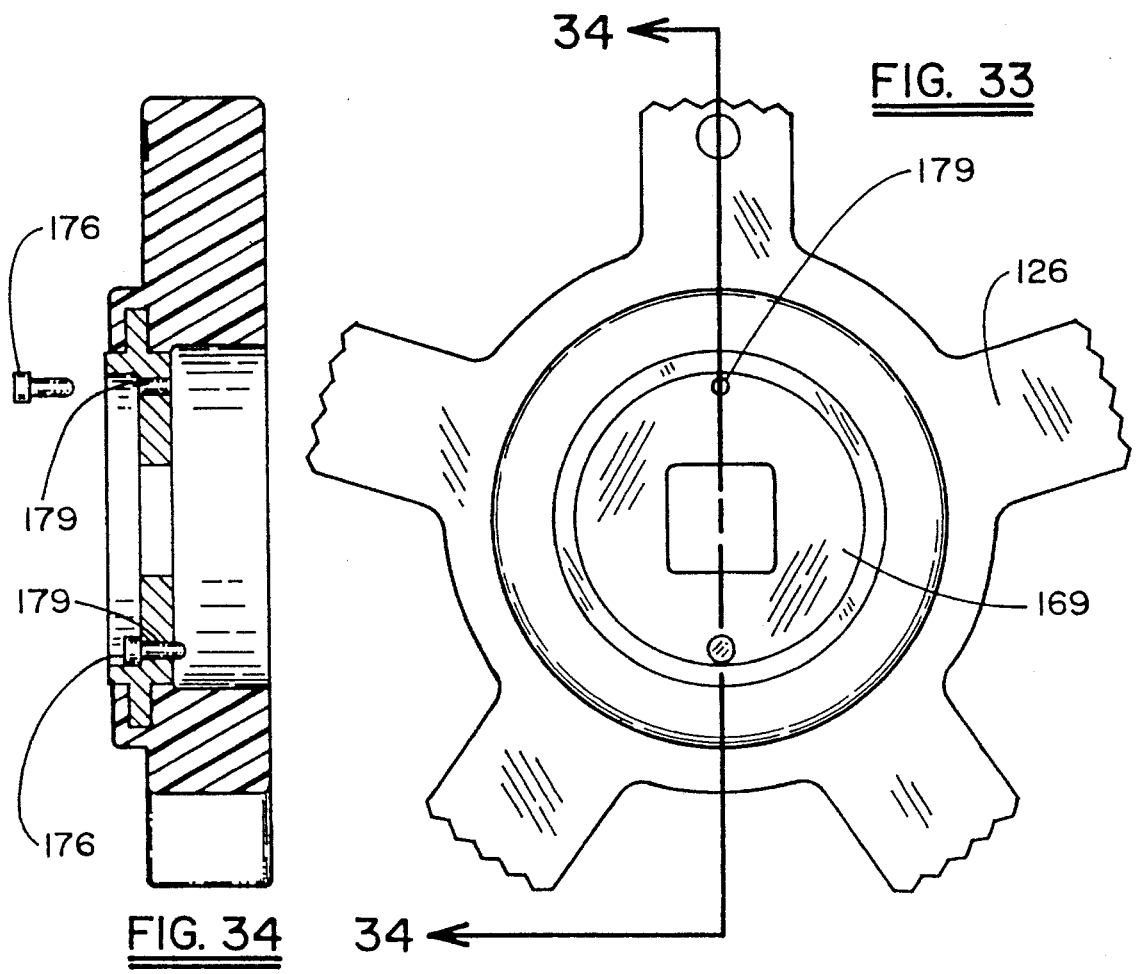

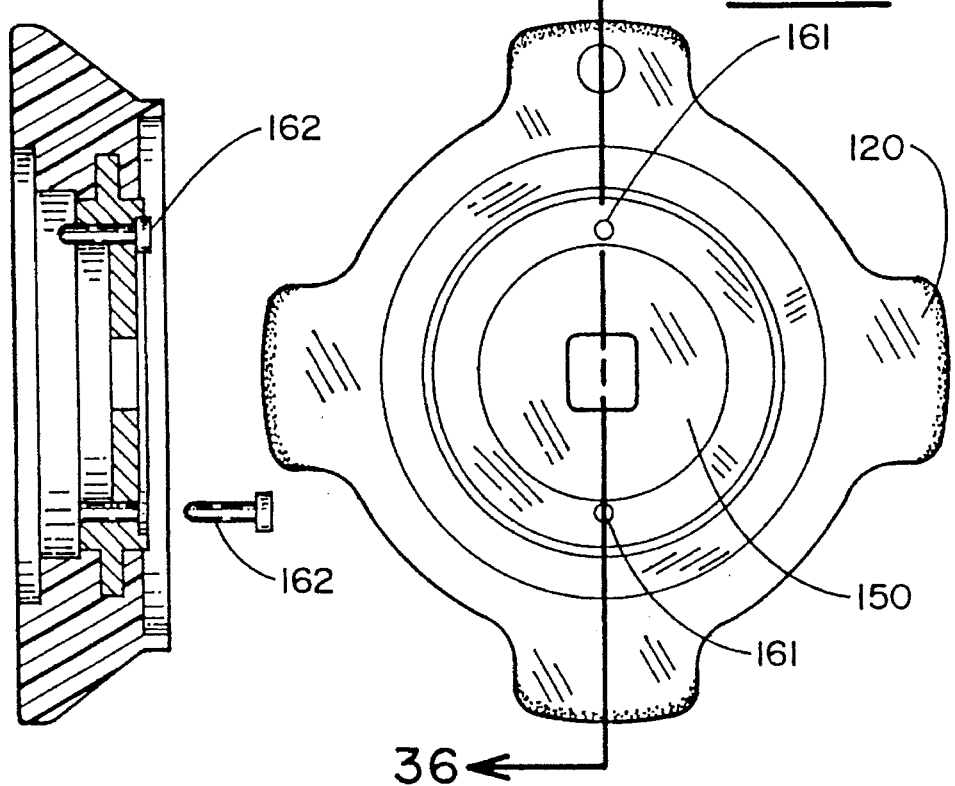
FIG. 35
FIG. 36
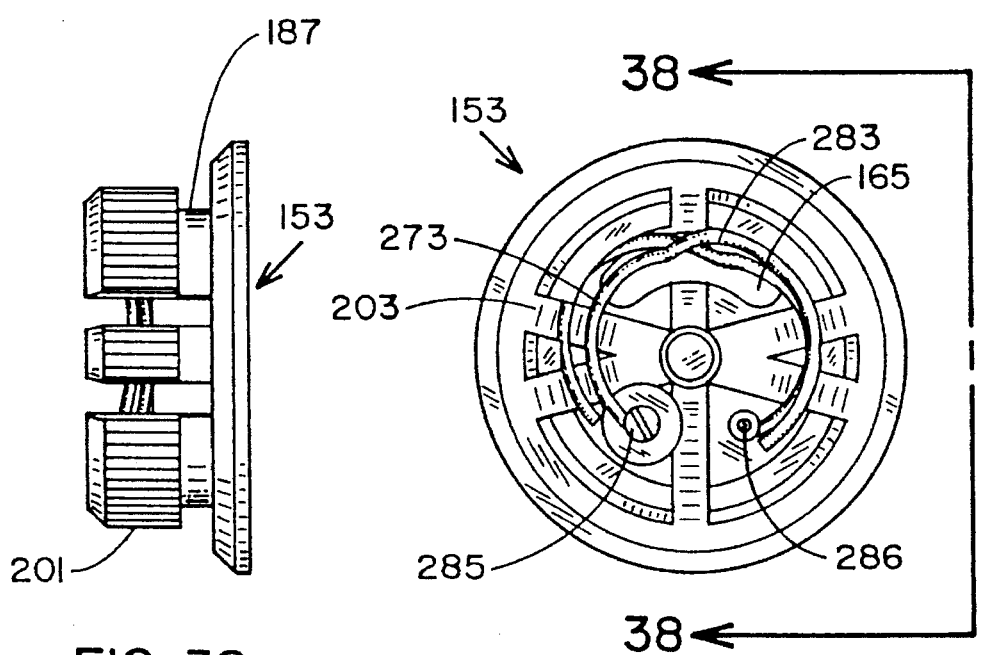
FIG. 37
FIG. 38

FLUID INSENSITIVE BRAKING FOR AN ENDOSCOPE

CROSS-REFERENCE TO RELATED APPLICATIONS

This application is a continuation-in-part of Ser. No. 08/200,383, filed Feb. 23, 1994, now U.S. Pat. No. 5,464,007.

BACKGROUND OF THE INVENTION

1. Field of the Invention

This invention relates in general to endoscopes and, in particular, to a steering mechanism for endoscopes. More specifically, but without restriction to the particular embodiments hereinafter described in accordance with the best mode of practice, this invention relates to a fully immersible, fluid-insensitive braking system for endoscopes.

2. Description of the Prior Art

The term endoscope shall be used herein in a generic sense to include broadly endoscopes, borescopes, and guide tubes. In many endoscopes the distal end of the insertion tube is capable of being articulated by a steering mechanism that includes a pair of external control wheels coupled to steering cables mounted inside the insertion tube. Rotation of one of the control wheels produces an up or down deflection of the distal tip of the insertion tube while rotation of the second control wheel produces a left or right deflection of the insertion tube tip. As can be seen, by operating the two control wheels, the distal end of the insertion tube can be pointed at a desired target within the range of the instrument or maneuvered through a tortuous path of travel.

The control wheels of the endoscope are typically affixed to superimposed shafts that are mounted on the control handle of the insertion tube. The shafts pass into the housing and are coupled to the steering cables by means of rack and pinion units or the like. It is necessary to apply a holding force to the steering cables in order to maintain the distal tip of the insertion tube at a desired fixed position. Heretofore this was generally achieved by friction pads that applied a friction force against some moving component of the steering section. Fluids, however, can lodge between a conventional brake pad and the moving component of the steering section which changes the frictional characteristics at the interface. A constant torque is needed which is high enough to hold the distal tip of the insertion tube at a desired target position-yet low enough to allow the distal tip of the insertion tube to self straighten during withdrawal from a confining space. A constant braking force also provides the user with a definite "feel" for the controls which facilitates rapid and accurate positioning of the insertion tube.

In the case of a medical endoscope, it is extremely important that the insertion tube be immersible in a cleaning fluid for sanitation purposes. This desired immersability heretofore required that the friction brake surfaces be completely isolated by fluid tight seals to prevent the pad from becoming wet. It is extremely difficult to properly seal these areas, and oftentimes the seal will deteriorate or break in time with usage. The seals are also expensive to fabricate and maintain and, because of their complexity, can themselves create contamination sites that are hard to keep clean.

U.S. Pat. No. 4,207,873 to Kruy discloses a braking system for an endoscope in which the traditional friction pad brakes are replaced by an incrementing ring having spaced apart indentations formed about its periphery that coact with a pair of pawls mounted in the companion control wheel. Each pawl includes a spring loaded ball which is seated in a set screw that is threaded radially into the hub of the control wheel. The wheel is slidably mounted upon a control shaft adjacent to the incrementing ring which in turn, is affixed securely to the shaft. To actuate the brake, the wheel is moved axially into engagement with incrementing ring. Each of the spring loaded balls must first snap over a retaining ring before being received in one of the indentations. Once engaged, the spring loaded detent ball places a prescribed holding force against the control wheel.

The incrementing rings and spring loaded balls of the Kruy system are mounted on the outside of the control handle and are thus open to the surrounding environment. Consequently, the relatively sensitive detent springs acting on the detent balls are exposed to moisture that can find its way into the spring housing set screw and thus cause corrosion of the spring. Any deterioration of the springs will lead to a change in the force exerted upon the steering system. Cleaning of the confined area behind the detent wall is also difficult.

SUMMARY OF THE INVENTION

An object of the present invention is to improve braking systems used in the steering mechanism of endoscopes and borescopes.

A further object of the present invention is to provide an open braking system for the steering system of an endoscope which does not require seals and which can be efficiently cleaned without adversely affecting the operation of the brake.

A still further object of the present invention is to provide a braking system for an endoscope having an open construction that permits cleaning fluids to reach all parts of the brake system.

Yet another object of the present invention is to provide a fluid insensitive and fully immersible braking system for an endoscope.

These and other objects of the present invention are attained by a steering mechanism for a flexible insertion tube of an endoscope that has an articulation section at its distal end, and deflection cables extending from the distal end to the proximal end thereof. A deflection control unit or steering mechanism comprises a control housing connected to the insertion tube at the proximal end thereof, and two control wheels are mounted for rotation upon the exterior of the housing. The control wheels are each connected by a shaft to two deflection cables for moving the distal end of the insertion tube in planes normal to one another when the control wheels are rotated. A brake disc is mounted on each shaft proximate an associated control wheel, and is movable axially toward and away from the adjacent control wheel. An actuator associated with each brake disc moves the brake disc in a first case, and in a second case moves the control wheel between a first position, wherein the brake disc is disengaged with its associated control wheel, and a second position wherein the brake disc is in braking engagement with the control wheel. A spring biases an engagement mechanism in each control wheel for maintaining a desired degree of braking engagement with the brake disc when the actuator is in the second position.

According to one aspect of the present invention the first and second control wheels each comprise a plurality of detent pins slidably mounted in holes bored therethrough, and the spring acts urges the pins toward the associated brake disc.

In accordance with another aspect of this invention, the brake discs have formed therein a series of depressions that sequentially receive ends of the detent pins when the control wheel is incrementally rotated, and when the actuator is in the second position to provide a resistive braking action.

According to yet another aspect of the invention, a disengaging spring associated with each brake disc urges the brake disc out of engagement with the control wheel when its associated actuator is in the first position, so that freewheeling operation of the control wheel is possible.

In still a further aspect of the present invention, the two shafts are concentrically arranged as an inner shaft and an outer shaft surrounding the inner shaft. A cylindrical support encircles a portion of the outer shaft and a second support passes axially through the inner shaft, Both supports are secured to the control housing. Seals are provided between each shaft and its respective support, and between the outer shaft and the control housing. The second support extends axially beyond an outer end of the inner shaft to provide an end section for supporting the brake and the control wheel thereon. Each support has a square cross-sectional section for slidably supporting the brake disc and the control wheel thereon, and also has a threaded section. The associated actuator is threaded thereupon, whereby turning the actuator will move the brake disc into and out of engagement with the detent pins of the associated control wheel. Each actuator includes a stop for stopping the actuator in the first position and the second position. Spring detents are provided for holding the actuator in each of the two extreme positions.

BRIEF DESCRIPTION OF THE DRAWING

For a better understanding of these and other objects of the present invention, reference is made to the detailed description of the invention which is to be read in conjunction with the following drawing figures, wherein:

FIG. 31 is a bottom view of the up/down brake disk of the embodiment shown in FIGS. 29 and 30;

FIG. 32 is a sectional view taken along lines 32—32 of FIG. 31;

FIG. 33 is an end view of the up/down control wheel of the embodiment shown in FIGS. 29 and 30;

FIG. 34 is a sectional view taken along lines 34—34 of FIG. 33 and further illustrating detent pins;

FIG. 35 is an end view of the right/left control wheel of the embodiment shown in FIGS. 29 and 30;

FIG. 36 is a sectional view taken along lines 36—36 of FIG. 35 similar to FIG. 34;

FIG. 37 is an end view of the actuating knob of the right/left control wheel shown in FIGS. 29 and 30; and FIG. 38 is a side elevation taken at lines 38—38 of the actuating knob shown in FIG. 37.

DESCRIPTION OF THE PREFERRED EMBODIMENT

Figure 1:
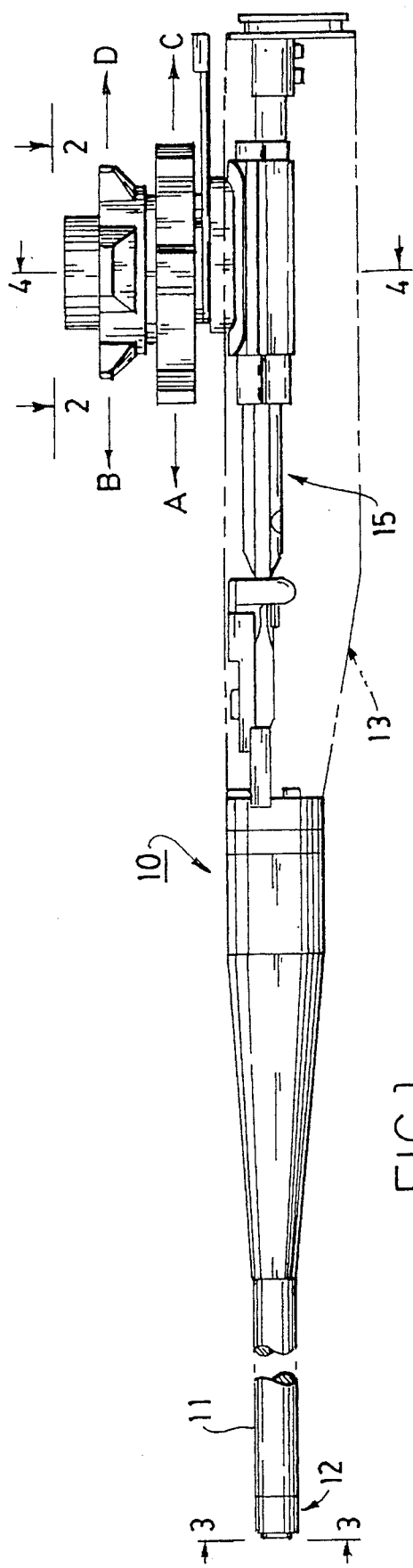
FIG. 1 is a partial side elevation of an endoscopic insertion tube with portions broken away to better illustrate the steering section thereof.
Figure 4:
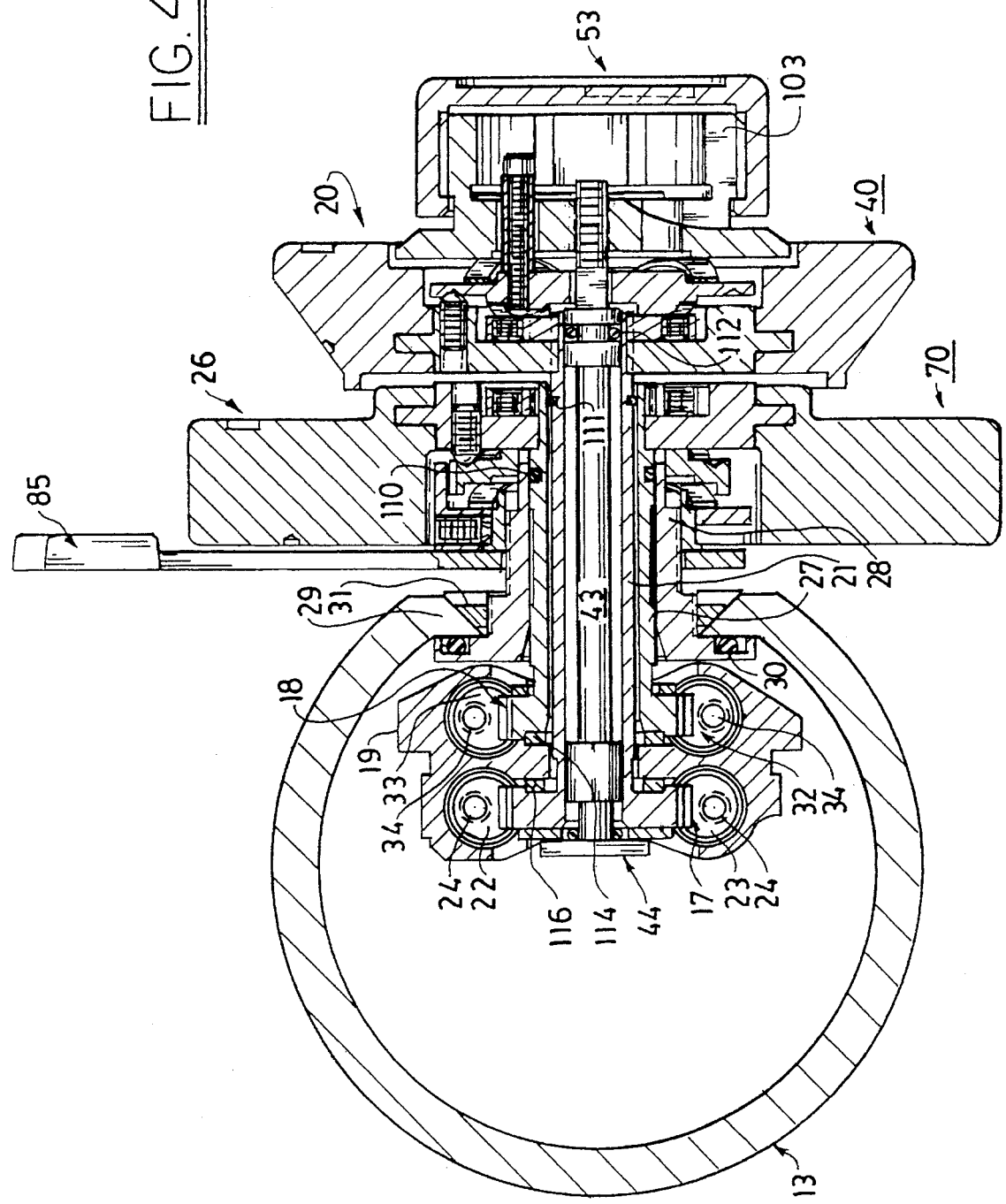
FIG. 4 is an enlarged sectional view taken along lines 4—4 in FIG. 1.

First embodiment:

Referring now to FIG. 1, there is shown an insertion tube 10 of the type employed in a video endoscope. The distal end 11 of the insertion tube is equipped with viewing head 12 that contains a CCD solid state imager (not shown). The proximal end of the insertion tube contains a hand engageable control housing 13 that is shown in phantom outline in FIG. 1. Mounted inside the housing is a steering mechanism generally referenced 15. As best seen in FIG. 4, the steering mechanism includes a pair of rack and pinion units 17 and 18 that are attached to displacement cables for articulating the distal end of the insertion tube. The outer rack and pinion unit 17 is connected to a first left/right control wheel 20 by means of a hollow inner shaft 21. The racks 22 and 23 of the unit 17 are attached to displacement cables 24 so that rotation of the control wheel 20 in directions B and D (FIG. 2) will cause the distal end of the insertion tube to be bent in a horizontal plane either to the right or the left of the axial centerline of the insertion tube.

The inner rack and pinion unit 18 is connected to a second up-down control wheel 26 via a second hollow shaft 27 that is housed inside a cylindrical support member 28 which forms part of the housing frame 19. The support member passes outwardly through the side wall 29 of the control housing and the opening closed by seal 30 and by the housing attachment ring 31. Racks 32 and 33 of the inner rack and pinion unit 18 are connected to displacement cables 34 whereby rotation of the second larger diameter wheel 26 in the A or C (FIG. 2) direction produces an up or down bending movement of the distal end of the insertion tube in a vertical plane. As can be seen, by manipulating the two control wheels, the distal end of the insertion tube can be directed in an infinite number of positions.

Figure 3:
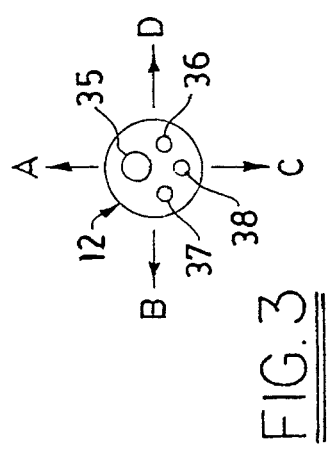
FIG. 3 is an end view of the distal tip of the insertion tube taken along lines 3—3 in FIG. 1.

As shown in FIG. 3, the viewing head 12 is mounted at the distal tip of the insertion tube and contains an optical window 35 through which the CCD imager can view a target within the range of the viewing optics. Light is directed onto the target area by means of a pair of fiber bundles 36 and 37 situated on either side of the viewing window. A biopsy channel 38 also opens to the target region through the front face of the distal tip and permits instruments to be inserted therethrough to carry out various well-known procedures. As noted above, by manipulating the control wheels, the front face at the distal tip of the insertion tube can be pointed accurately at a target located in a remote and generally inaccessible region or the tube can be guided through tortuous passages.

Figure 2:
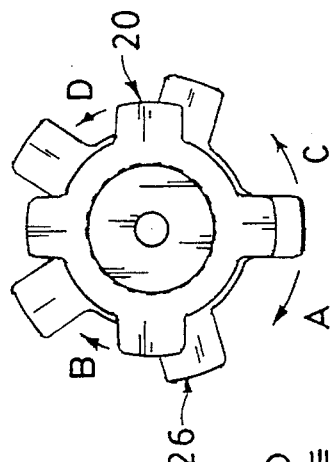
FIG. 2 is a top view showing the control wheels that are mounted upon the control handle of the insertion tube.

The left/right control wheel 20 is placed on the outside of the up/down control wheel 26. As illustrated in FIG. 2, the wheels each have a different size diameter and the geometry of the wheels are also different. The outer wheel is smaller in diameter and contains four radially disposed spokes while the inner wheel has a larger diameter and contains five equally spaced spokes extending radially from the hub of the wheel. A person using the endoscope can rapidly identify each wheel by touch, thus allowing the user to continually view the target region on the video screen (not shown) to which the CCD imager is electrically connected.

With further reference to FIGS. 22–28 there is shown a sub assembly of the left/right control wheel system generally referenced 40. The sub assembly includes the previously noted left/right control wheel 20 which is secured to the hollow shaft 21 for rotation therewith. A pinion 41 is mounted on the inboard end of the shaft and mates with the rack 22 and 23 of the outer rack and pinion unit 17 (FIG. 4). A stationary support shaft 43 is contained within the hollow shaft 21 and is secured to the housing frame 19 by means of an end bracket 44. The shaft 21 is rotatably mounted upon the support shaft by means of bearings 45 and 46 whereupon the left/right control shaft can be freely rotated by turning the control in either direction B or D as seen in FIG. 2. In assembly, the control wheel is mounted on a square section 47 at the end of the hollow shaft 21 and is tightened against a shoulder 48 formed on the shaft. The wheel is held tightly against the shoulder by means of a jam nut 49 that is threaded onto the shaft behind the wheel and tightened against the end face of the wheel hub 50. Set screws 51—51 are threaded through the jam nut and are tightened down against the hub to further secure the wheel to the shaft.

The right end of the support shaft 43 is equipped with a threaded shank 52 upon which an actuator knob 53 is mounted. Turning the actuator knob upon the shank causes the knob to move axially toward or away from the inner end face of the left/right control wheel hub 50. A floating brake disc 55 (FIGS. 26 and 27 having a square shaped centrally located hole 57) is mounted on a square section 56 of the support shaft 43 (FIGS. 24 and 25) so that the brake disc can move axially between the actuator knob and the hub of the left/right control wheel. The threaded shank of the support shaft is provided with a multiple thread whereby turning of the actuator knob will produce rapid axial movement of the knob toward or away from the control wheel 20.

A pair of wave washer springs are mounted on either side of the brake disc 55. The spring rate of wave washer 59 is greater than that of wave washer 60, the reason for which will be explained in greater detail below. In practice, each of these wave washers can consist of several stacked individual wave washers.

A ratchet mechanism is made up of detent pins 62 (preferably three) and a series of circumferentially spaced depressions 63—63 formed in the face of the brake face that is adjacent to the control wheel. The detent pins are staked into the hub of the control wheel and each has a rounded tip that is receivable into the circumferentially spaced depressions formed in the brake disc. Turning the actuating knob in one direction will cause the wave washer springs to be compressed and will force the brake disc into engaging contact with the detent pins, thus placing a biasing force upon the ratchet mechanism. This in turn places a braking torque upon the control wheel and a braking force on the associated displacement cable. The torque needed to do this depends on the net axial engagement force of the two springs, the geometry of the detent pin tips and the receiving depressions, the radial location of the depressions, and to a much lesser extent, upon the friction coefficient of the sliding surfaces of the ratchet mechanism. The braking torque achieved can be varied by changing the axial travel of the actuating knob and/or by changing the relative stiffness of the springs.

Figure 23:
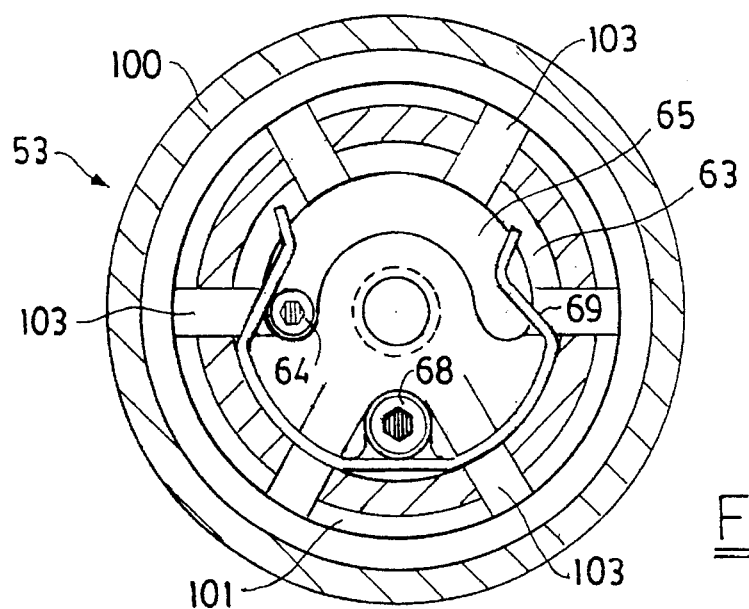
FIG. 23 is a sectional view taken along lines 23—23 in FIG. 22.
Figure 24:
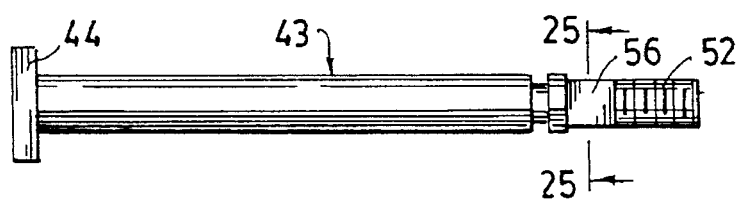
FIGS. 24 and 25 are two views of the left/right control wheel shaft.
Figure 25:
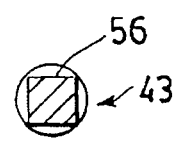
Figure 26:
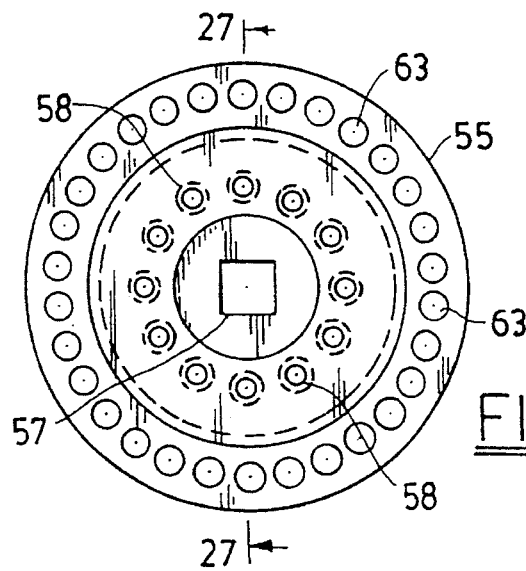
FIGS. 26 and 27 are two views of the left/right brake disc.
Figure 27:
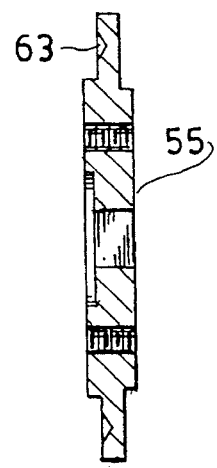
Figure 28:
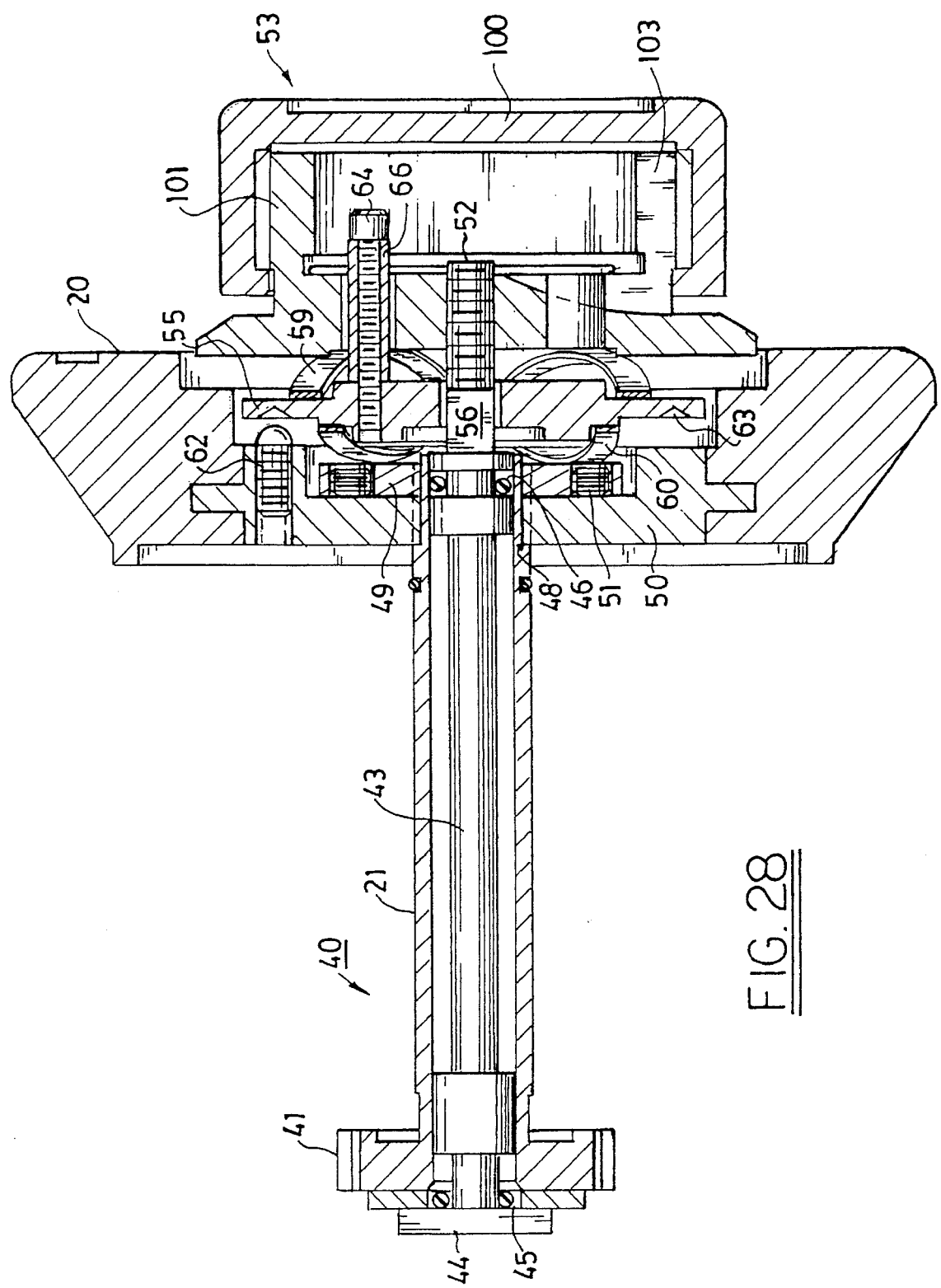
FIG. 28 is a sectional view similar to that of FIG. 22 showing the left/right brake disc in a disengaged position.

Turning now to FIG. 23, there is shown a stop mechanism 63 for regulating the amount of axial travel afforded the actuator knob. The stop mechanism includes an axially disposed stud 64 which is threaded into one of a series of threaded holes 58—58 formed in the brake disc (FIG. 26). The stud is arranged to pass upwardly through an arcuate shaped slotted hole 65 formed in the hub of the actuator knob. A cylindrical sleeve 66 surrounds the stud 64 (FIG. 28). The slotted hole subtends an arc of about 180° thus permitting the knob to be advanced or retracted freely along the threaded shank of the support shaft about one-half a turn. A spring 69 is mounted in the hub of the actuator knob and is contoured to hold the stud in the extreme brake disc engaging and disengaging positions against the end walls of the slotted hole. The spring is attached to the actuator knob by screw 68.

When the stud is bottomed against one end wall of the slotted hole, the actuator knob is retracted to the position shown in FIG. 28 and the compressive force on spring 59 is relieved. The softer spring 60 will now take over and push the brake disc away from the control wheel hub, thus disengaging the ratchet mechanism. This allows the control wheel to turn freely and smoothly during the steering operation. Turning the actuator knob in the opposite direction will bring the stud against the other end wall of the slotted hole, thus compressing the spring 59 and producing an engagement of the ratchet as explained above. At this time, the spring 59 acting through the ratchet mechanism will place a braking force against the left/right control wheel thus holding the distal tip of the insertion tube at a desired position in the horizontal plane. The control wheel can be incremented in either direction between the depressions in the brake disc by applying sufficient torque to the wheel to overcome the spring holding force.

Figure 21:
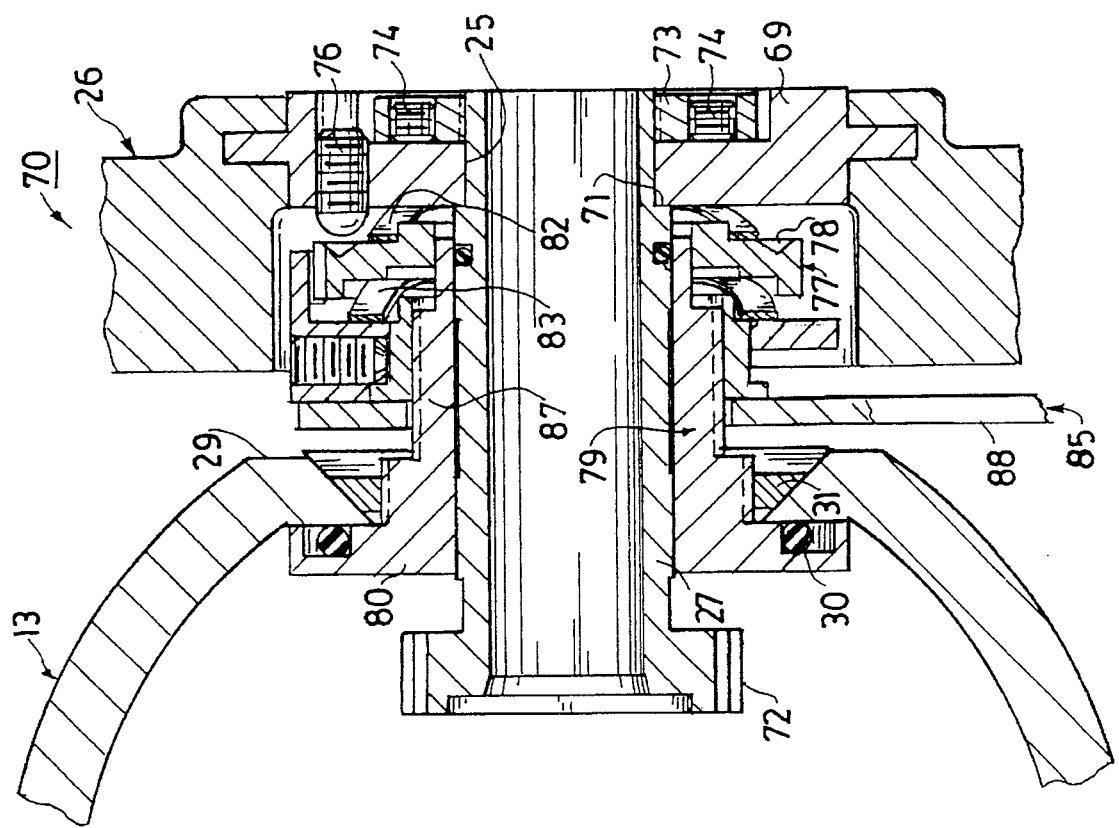
FIG. 21 is a sectional view similar to that of FIG. 5 showing the up/down brake disc in a disengaged position away from the adjacent up/down control wheel.
Figure 22:
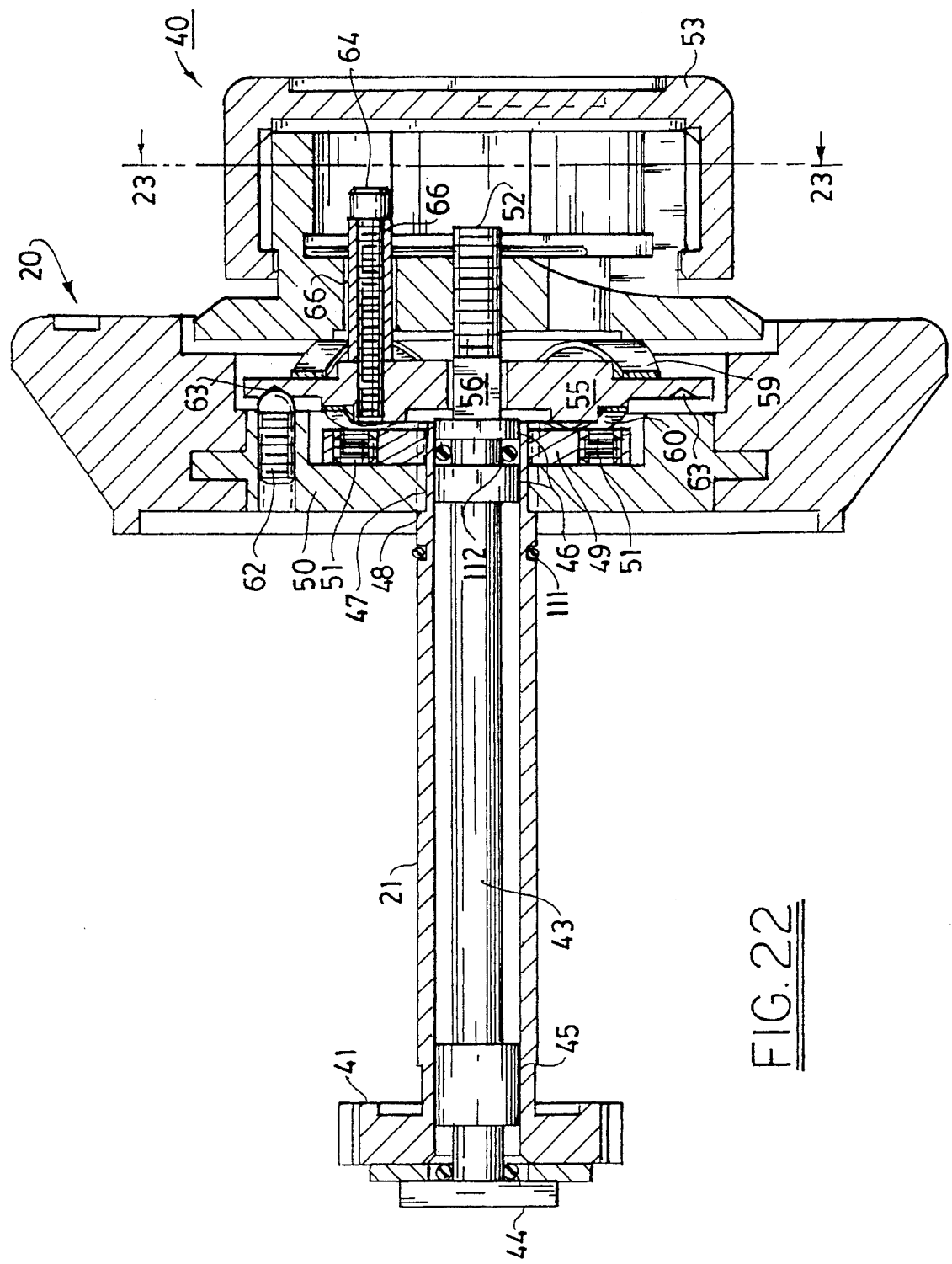
FIG. 22 is a side elevation in section showing the left/right control wheel and an associated brake disc in engagement with the adjacent control wheel.

With further reference to FIGS. 5–21 there is shown the sub assembly of the up/down control system which is generally referenced 70 (FIG. 21). The up/down control system operates in much the same manner as the left/right control system to apply a braking torque to the steering mechanism and thus hold the distal end of the insertion tube in a desired position in a vertical plane. The up/down control wheel 26 is secured for rotation to a square section 25 at the end of the hollow shaft 27 that surrounds the previously noted left/right control shaft 21. A pinion 72 is mounted on the inner end of the shaft and, as explained above, is arranged to engage a pair of racks for moving the up/down displacement cable 34 (FIG. 4) contained within the insertion tube. The control wheel is mounted on the outer end of the shaft and is tightened against a raised shoulder 71 from on the shaft. A jam nut 73 is threaded onto the shaft behind the hub of the control wheel to lock the hub against the shoulder. Set screws 74—74 are used to hold the jam nut securely against the control wheel in assembly.

Three detent pins 76 are staked into the hub 69 of the control wheel and extend inwardly from the hub toward the up/down brake disc 77. A series of circumferentially spaced depressions 78—78 are formed in the front face of the brake disc for receiving the contoured tips of the detent pins 76.

A cylindrical support member 28 surrounds the up/down control shaft. The support member is equipped with a radially expanded mounting flange 80 that is secured to the inside wall of the control housing by the housing attachment ring 31. The main body section of the support cylinder passes out of the housing through an opening in the housing side wall.

Figure 6:
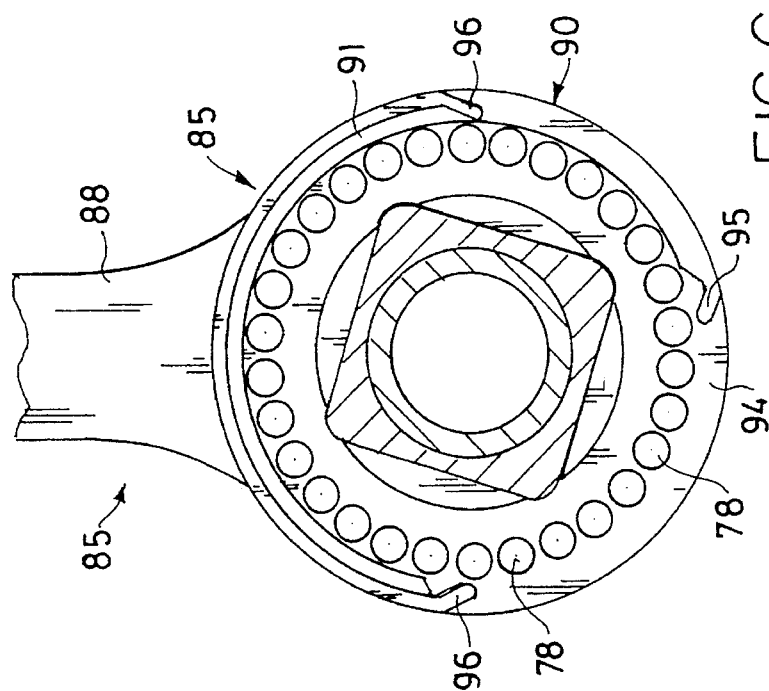
FIG. 6 is a sectional view taken along lines 6—6 in FIG. 5.

The up/down brake disc 77 is slidably mounted on a flat section 81 (FIG. 7) of the support cylinder so that it can move axially towards and away from the hub of the up/down control wheel 26. A pair of wave washer springs 82 and 83 are positioned on either side of the brake disc. Spring 82 has a lower spring rate than spring 83 and is positioned between one face of the brake disc and the hub 69 of the control wheel 26. The other (heavier) spring 83 is positioned between the disc and an actuator unit generally referenced 85 (FIG. 6). In practice, each of these wave washer springs can consist of several stacked individual wave washers.

As best seen with reference to FIGS. 6–20, the actuator unit 85 includes a cylindrical hub 86 (FIG. 14) having internal threads that permit the hub to be screwed onto the threaded section 87 (FIG. 7) on the support member 28. A lever arm 88 (FIG. 6) is secured to the front face 89 (FIG. 12) of a shroud 90 to clamp the hub therebetween. A yoke 91 which forms part of the shroud extends outwardly from the shroud. In assembly, the yoke overlies and partially encompasses the up/down brake disc.

Figure 9:
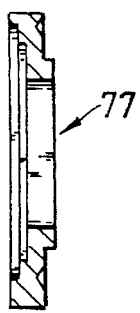
FIG. 9 is a side view in section of the up/down brake disc.
Figure 10:
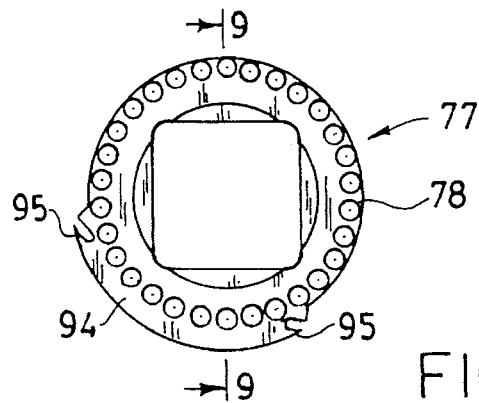
FIG. 10 is a front view of the up/down brake disc.
Figure 13:
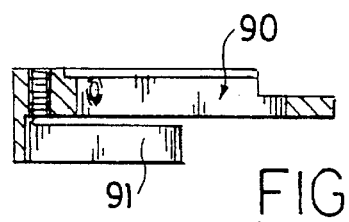
FIGS. 11–13 are three views of the up/down brake actuator cover.
Figure 11:
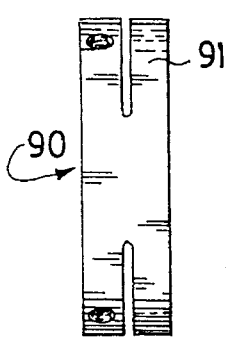
Figure 12:
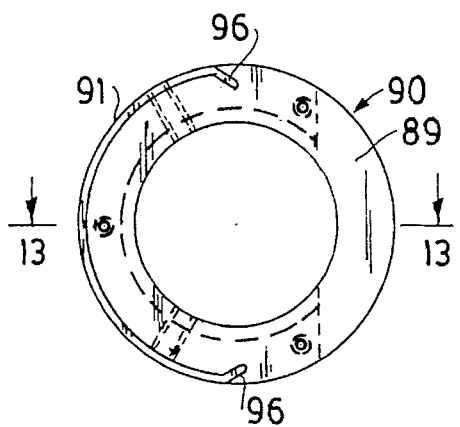
Figure 14:
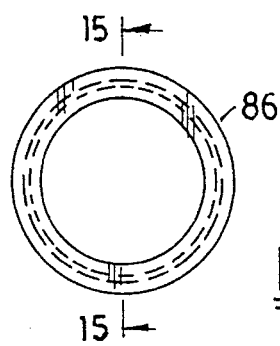
FIGS. 14 and 15 are two views of the up/down brake actuator arm hub.
Figure 15:
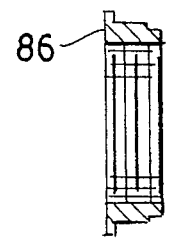
Figure 16:
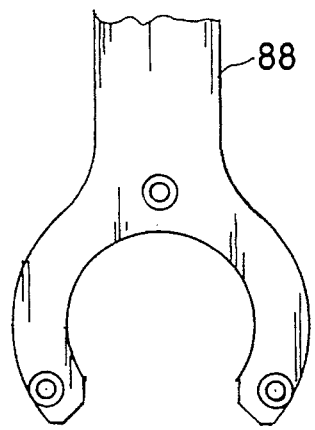
FIGS. 16 and 17 are two views showing the up/down actuator arm.
Figure 17:
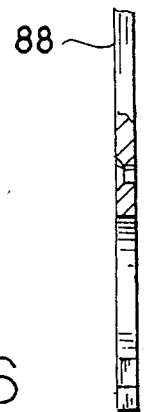
Figure 18:
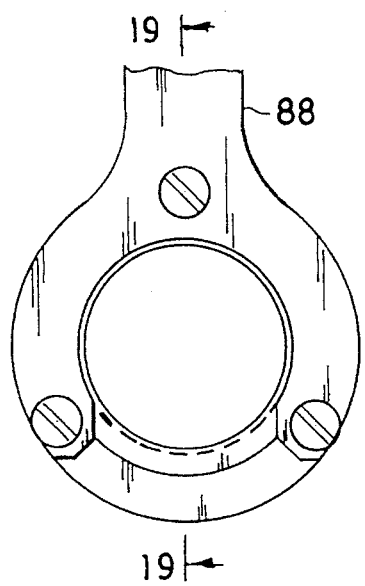
FIGS. 18–20 are three views showing the up/down brake actuator arm assembly.
Figure 19:
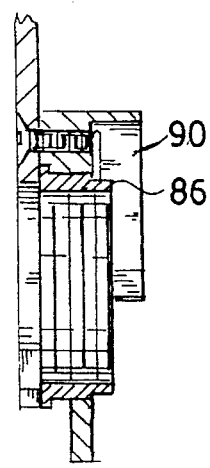
Figure 20:
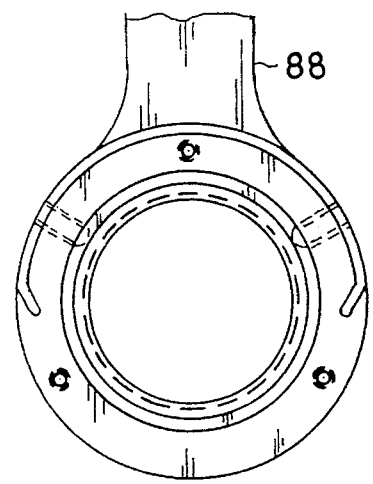

As best illustrated in FIGS. 9 and 10, the brake disc 77 has a radially extended section 94 that contains a pair of slots 95 situated at each end of the radially extended section 94. The slots are adapted to receive therein tabs 96—96 that are carried on the circumferentially opposed ends of the shroud (FIG. 12).

Figure 5:
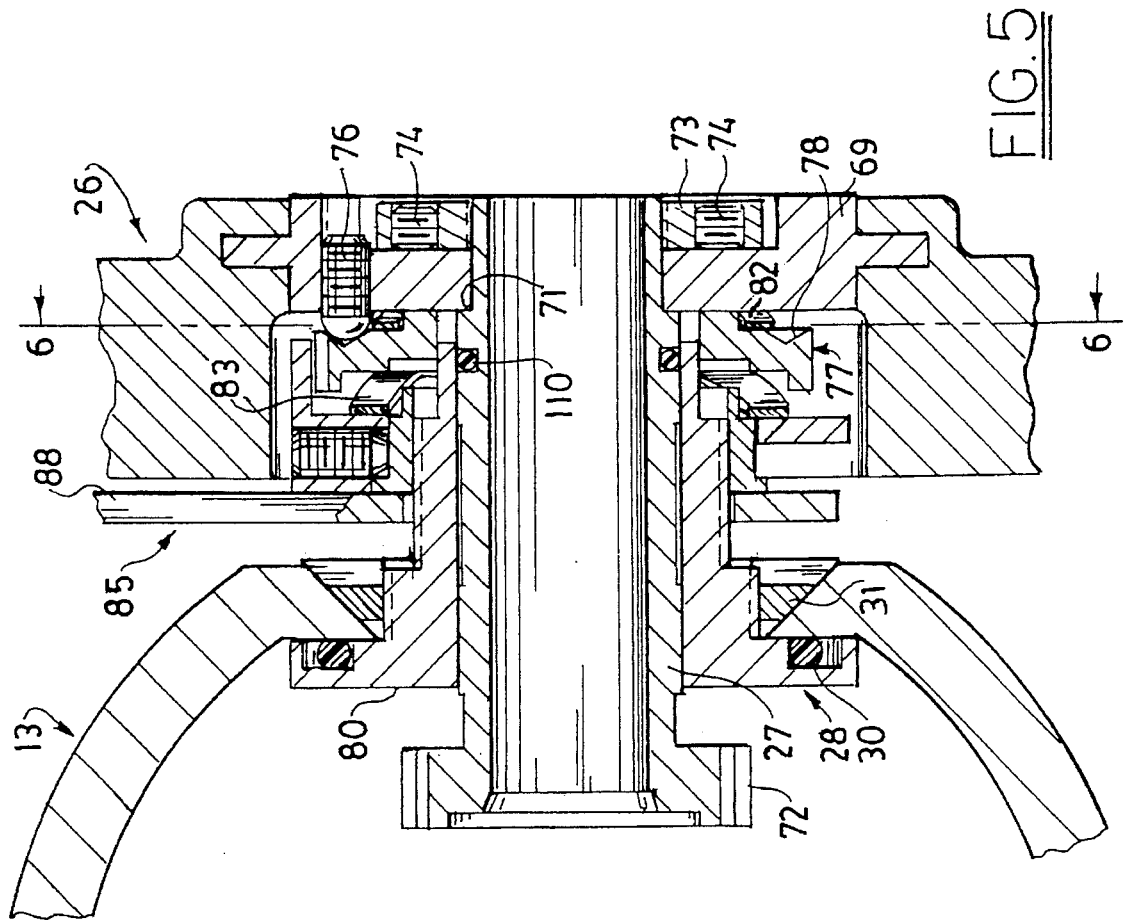
FIG. 5 is a further enlarged sectional view showing the up/down control wheel and a brake disc associated therewith in a control wheel engaging position.
Figure 7:
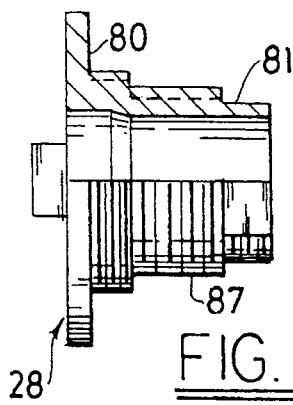
FIG. 7 is a side elevation of a hub for mounting the up/down control wheel upon the control housing.
Figure 8:
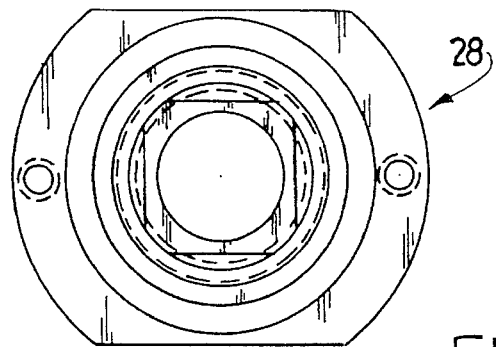
FIG. 8 is an end view of the hub shown in FIG. 7.

In operation, turning the lever arm will cause the actuator unit to move axially toward or away from the control wheel 26 (FIG. 5 and FIG. 21). The amount of rotation afforded the actuator unit is regulated by the circumferential spacing between the two slots formed in the brake disc. Turning the lever in one direction so that a tab on the shroud seats in one slot will advance the actuator unit toward the up/down control wheel thus compressing the springs 82 and 83 (FIG. 5). This, in turn, will cause the depressions 78 formed in the brake disk to be seated on the pins 76, thus placing a restraining force on the up/down deflection cable. As in the case of the left/right control system subassembly, rotation of the control wheel occurs when the applied torque is sufficient to overcome the spring pressure holding the detent pins in the depressions. Accordingly, the deflection cable can be incremented in either direction by moving the pins between adjacent depressions.

Rotating the lever arm in the opposite direction will cause the actuator unit to move away from the control wheel (FIG. 21). The pressure on the heavy spring 83 is released and the softer spring is now allowed to push the brake disc away from the detent pins, thus disengaging the ratchet mechanism. With the ratchet disengaged, the up/down control wheel is able to move freely.

With further reference to FIGS. 23 and 28, actuator knob 53 includes an outer cylindrical cap 100 that is press fitted upon an inner rotor 101 which as is in turn threaded upon the outer end of support shaft 43. A series of spaced apart drain channels 103 are formed in the raised side wall of the rotor that allow any fluid trapped under the cap 100 to efficiently drain from beneath the knob thus rendering this region fluid free in the event the instrument is exposed to cleansing fluids or the like.

As depicted in FIG. 4, the present control knob assembly, because of its fluid insensitive brake system, is able to utilize a very simple sealing arrangement to prevent cleansing fluids and the like from entering the control housing 13 of the instrument when compared to other endoscopic braking systems. As shown in FIG. 4, the sealing arrangement includes an O-ring seal 30 that acts between the support member 28 and the inner wall of the control housing. A series of two further O-rings 110 and 111 are mounted along the two pinion shafts 21 and 27 and finally an end O-ring seal 112 is mounted between the support shaft and inner shaft 21. Seals 110–112 prevent fluids from entering the control housing from between the shafts.

The inner shaft O-ring 111, under certain conditions, may transmit torque between the pinion shafts 21 and 27. As a result, rotation of one shaft may tend to cause the other shaft to rotate also. This can be avoided by eliminating O-ring 111 and, instead, placing an O-ring 114 between the inboard end of shaft 27 and the housing frame 19 and another O-ring 116 between the inboard end of shaft 21 and the housing frame 19.

Figure 29:
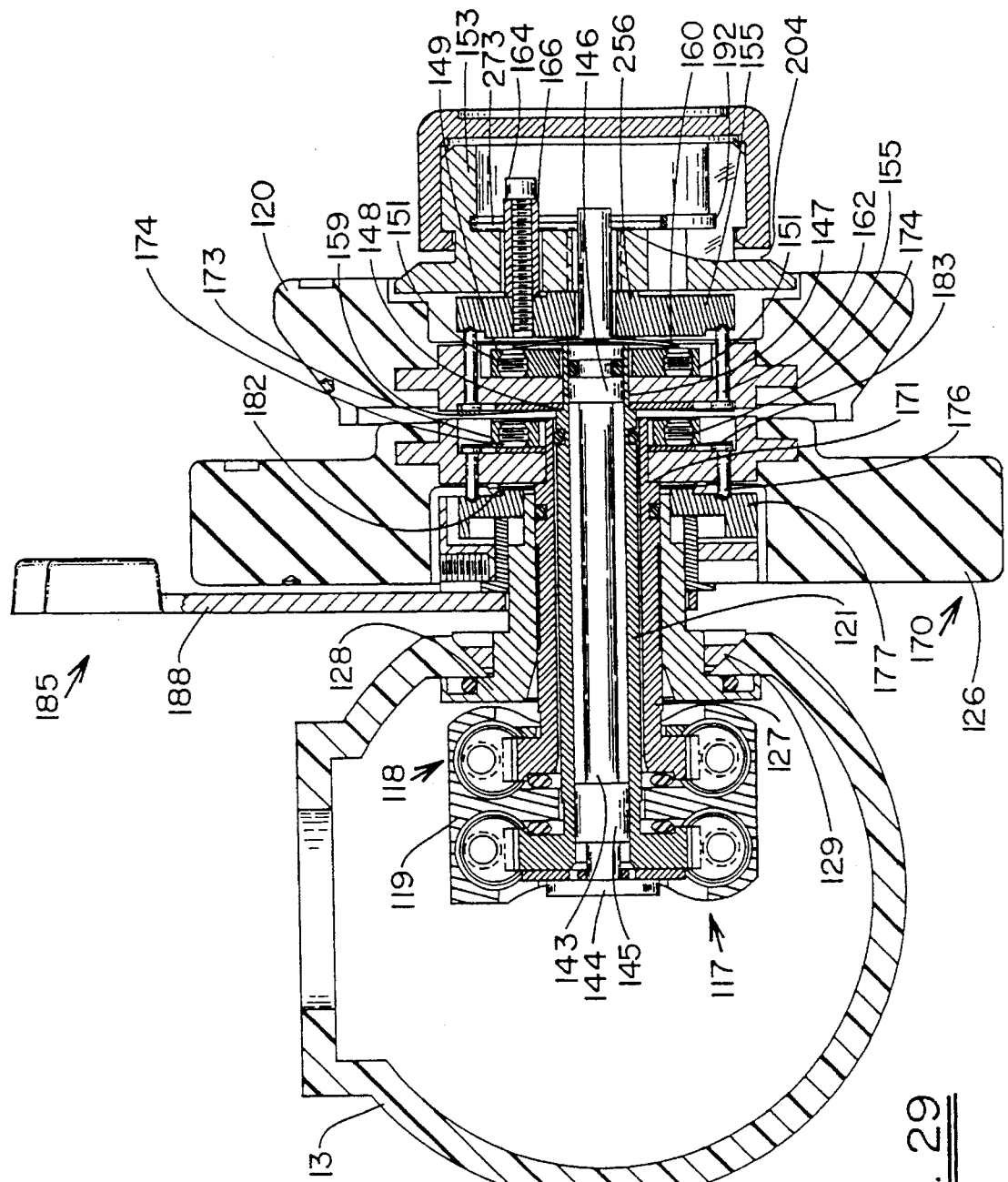
FIG. 29 is a sectional view of an alternate embodiment of the invention taken in a plane similar to FIG. 4.
Figure 30:
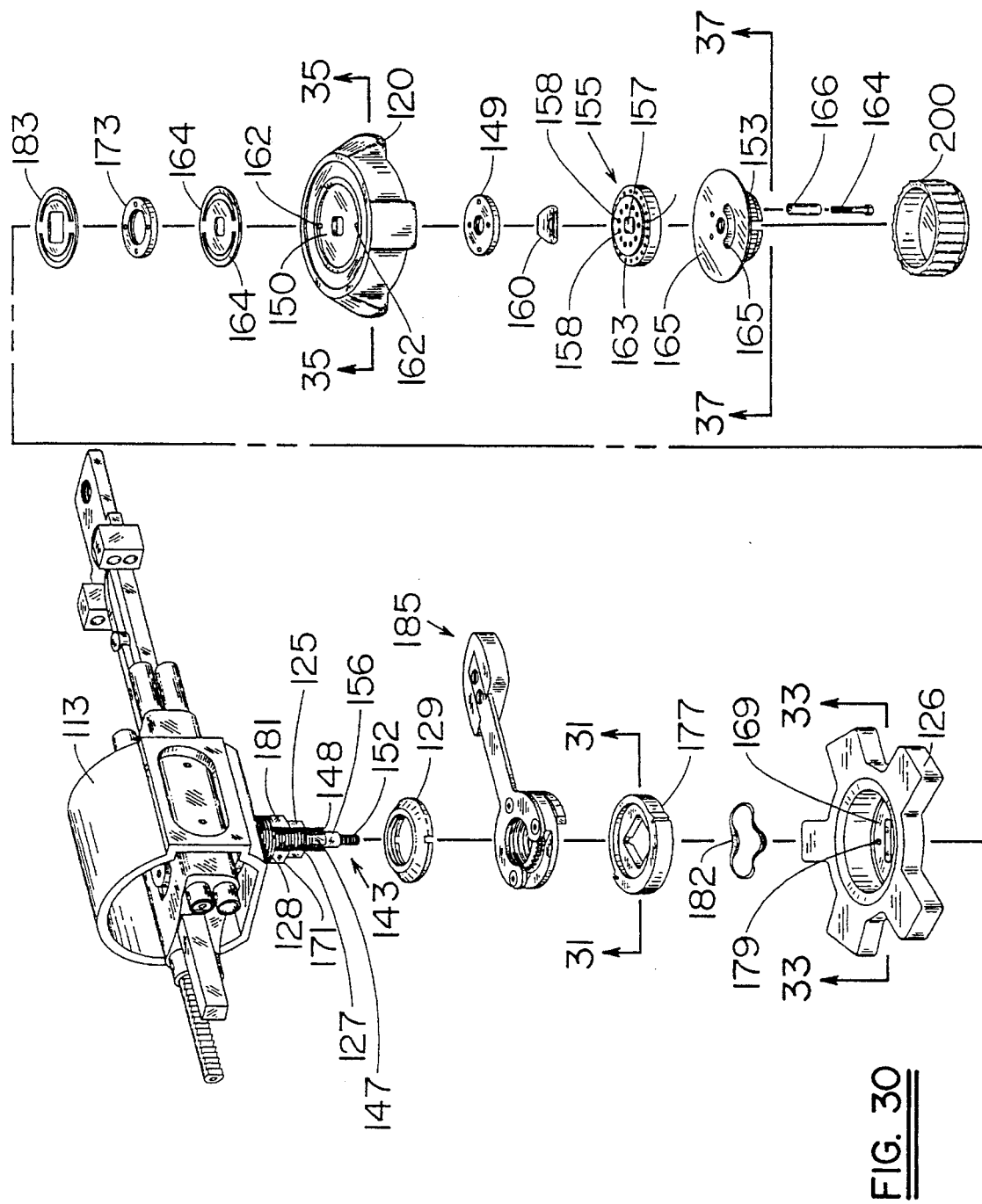
FIG. 30 is an exploded view of the braking mechanisms in the embodiment of FIG. 29.

Second embodiment:

Turning now to FIGS. 29–30, there is shown an alternate embodiment of the invention, wherein parts identical or analogous to those of the first embodiment have reference numerals advanced by 100. The alternate embodiment possesses a control housing 113 that can be engaged and operated with one hand, rack-and-pinion units 117, 118, and a frame 119 disposed in the housing. The rack-and-pinion units are controlled by hollow shafts 121, 127. A stationary support shaft 143 is contained within the hollow shaft 121 and is secured to the housing frame 119 by means of an end bracket 144. Bearings 145, 146 support the hollow shaft 121. An externally threaded cylindrical support flange 128 extends through the housing and surrounds the up/down control shaft. An internally threaded lock ring 129 secures the control housing 113 against one shoulder of the cylindrical support flange 128. These components are all identical to corresponding parts of the first embodiment, and will not be further discussed.

In assembly, a left/right control wheel 120 is mounted on a square section 147 near the end of the hollow shaft 121 and is disposed between an internally threaded retaining ring 149 and a strong disc spring 159. The disc spring also is carried by the square section 147, and bears against a shoulder 148 formed on the shaft, its outer crescentic rim portions 164— 164 working against the heads of two floating detent pins 162—162 (FIG. 36) that extend through holes 161—161

(FIG. 35) bored through the hub 150 of the control wheel 120 (FIG. 35). The action of the disc spring 159 urges the pins 162—162 through the control wheel 120 for reasons that will be explained below. Set screws 151—151 are threaded through the retaining ring 149 and are tightened down against the shaft 121 to hold the retaining ring 149 in a fixed axial position.

The end of the support shaft 143 that is remote from the end bracket 144 is equipped with a threaded shank 152 upon which an actuator knob 153 is mounted. Turning the actuator knob upon the shank causes the knob to move axially toward or away from the inner end face of the left/right control wheel hub 150. A brake disc 155 having a square shaped centrally located hole 157 is mounted on the square section 156 of the support shaft 143. The brake disk 155 is axially slidable on the square section 156, but during braking is held in position against the face 154 of the actuator knob 153, and does not oscillate as in the first embodiment. A small step 256 on the surface of the brake disk that is in contact with the face 154 is positioned to prevent cocking of the brake disc. The washer spring 160 urges the brake disc 155 away from the retaining ring 149 when the brake is disengaged.

A ratchet mechanism is made up of two diametrically opposed detent pins 162—162 and a series of circumferentially spaced depressions 163—163 formed in the brake surface that faces the control wheel 120. As explained above, the detent pins float axially within the hub of the control wheel and each has a rounded tip that is receivable into the circumferentially spaced depressions 163—163 formed in the brake disc.

The disc spring 159 is at all times under load to preload the heads of the detent pins 162—162. Turning the actuator knob 153 in one direction will force the brake disc into engaging contact with the detent pins 162—162. This in turn places a braking torque upon the control wheel and a braking force on the associated displacement cable. The torque needed to do this depends on the net axial engagement force of the disc spring 159, the geometry of the detent pin tips and the receiving depressions, the radial location of the depressions, and to a much lesser extent, upon the friction coefficient of the sliding surfaces of the ratchet mechanism. The braking torque achieved can be varied by changing the axial travel of the actuator knob, the stiffness of the disc springs, or the preload of the disc spring on the heads of the detent springs 162—162.

When the actuator knob 153 is turned in the opposite direction, the above sequence is reversed. When the actuator knob withdraws sufficiently, the washer spring 160, working against the retaining ring 149, urges the brake disc 155 away from the retaining ring 149, and disengages the rounded tips of the detent pins 162—162 from the depressions 163—163, to allow free-wheeling operation of the control wheel 120.

As best shown in FIGS. 29, 30, and 37, a stop mechanism regulates the amount of axial travel afforded the actuator knob 153. The stop mechanism includes an axially disposed stud 164 which is threaded into one of a series of threaded holes 158—158 formed in the brake disc 155. The stud is arranged to pass upwardly through an arcuate shaped slotted hole 165 formed in the hub of the actuator knob. A cylindrical sleeve 166 surrounds the stud 164. The slotted hole subtends an arc of about 90° thus permitting the knob to be advanced or retracted freely along the threaded shank of the support shaft about one-quarter of a turn. Two locking springs 273, 283 are mounted in the hub of the actuator knob and are contoured to hold the stud in the extreme brake disc engaging and disengaging positions against the end walls of the slotted hole. The springs seat in notch 192 which is formed circumferentially in the inner surface of side wall 187 (FIG. 38) of the actuator knob 153. Spring 273 is also retained in position by a screw fastener 285, about which the terminal portion of the wire spring 273 is wrapped. Spring 283 is similarly also retained in position by screw fastener 286 about which the terminal portion of the wire spring 283 is wrapped. The locking action of the springs 273, 283 upon the stud 164 provides a tactile sensation for the operator at the extreme positions of travel of the actuator knob 153.

With further reference to FIGS. 30 and 38, an outer cylindrical cap 200 is press fitted upon an outer knurled cylindrical surface of actuator knob 153. A series of spaced apart drain channels 203 are formed in the raised side wall 187 of the actuator knob that allow any fluid trapped under the cap 200 to efficiently drain from beneath the knob through the gap 204 (FIG. 29), thus rendering this region fluid free in the event the instrument is exposed to cleansing fluids or the like.

Referring to FIGS. 29–35, the sub assembly of the up/down control system is generally referenced 170 (FIG. 29). The up/down control system operates in much the same manner as the up/down control system of the first embodiment. The up/down control wheel 126 is secured for rotation to a square section 125 at the end of the hollow shaft 127 that surrounds the previously noted left/right control shaft 121. The control wheel 126 is mounted on the outer end of the shaft and is tightened against a raised shoulder 171. A retaining ring 173 is threaded onto the shaft behind the hub of the control wheel 126 to lock the hub against the shoulder 171. Set screws 174—174 are used to hold the retaining ring 173 securely against the control wheel 126 in assembly.

As best shown in FIGS. 29, 33 and 34, two detent pins 176—176 float within holes 179—179 formed in the hub 169 of the control wheel 126 and extend inwardly from the hub toward the up/down brake disc 177. A series of circumferentially spaced depressions 178—178 (FIG. 32) are formed in the front face of the brake disc for receiving the contoured tips of the detent pins 176.

An actuator unit, referenced generally at 185 (FIG. 29) is constructed similarly to that of the first embodiment, particularly in the details of its engagement with the up/down brake disc 177.

The up/down brake disc 177, is mounted on a flat section 181 (FIG. 30) of the support cylinder. As shown in FIGS. 32 and 33, the brake disc 177 has a very similar construction to the up/down brake disc 77 of the first embodiment, except that the brake disc 177 has been redesigned to contact the lever of the actuator unit 185 directly. A radially extended section 194 contains a pair of slots 195—195 situated at each end of the radially extended section 194. The slots 195—195 are adapted to receive therein tabs of the shroud of the actuator unit 185 in the same manner as shown in the actuator unit 85 of the first embodiment.

A wave washer spring 182 is positioned between the brake disc 177 and the hub of the control wheel 126. In practice, the wave washer spring 182 can consist of several stacked individual wave washers. A disc spring 183 is positioned between the retaining ring 173 and the hub 169 of the control wheel 126.

In operation, as in the first embodiment, turning the lever arm 188 will cause the actuator unit 185 to move axially toward or away from the control wheel 126 (FIG. 5 and FIG. 21). The amount of rotation afforded the actuator unit is regulated by the circumferential spacing between the two slots 195—195 formed in the brake disc. Turning the lever in one direction so that a tab on the shroud seats in one slot will advance the actuator unit 185 and urge the up/down brake disc 177 against the control wheel 126. This, in turn, will cause the depressions 178 formed in the brake disk to be seated on the rounded tips of the two diametrically opposed detent pins 176—176, thus placing a restraining force on the up/down deflection cable. As braking is increased, the depressions 178 are urged with increasing force against the detent pins 176—176. The brake disc 177 is held against the lever arm assembly, and does not float as in case of the first embodiment.

Rotating the lever arm in the opposite direction will cause the actuator unit 185 to move away from the control wheel 126. The pressure on the detent pins 176—176 is released and the wave washer spring 182 is now allowed to push the brake disc away from the detent pins, thus disengaging the ratchet mechanism. With the ratchet disengaged, the up/down control wheel is able to move in a free-wheeling mode.

As in the case of the left/right control system just described, the disc spring 183 works directly against the heads of the detent pins 176—176 and the retaining ring 173 to effect a preload on the pins. Direct preloading of the detent pins 176—176 and 162—162 has the advantage, compared to the first embodiment, of increasing the ratcheting torque obtained when the brake discs contact the detent springs. It will be evident that braking action is achieved with axial motion of the detent pins rather than with axial motion of the brake discs. As the brake discs are fixed axially in position, there need be no concern that the brake discs could bind on their respective shafts when the actuating units are advanced or when ratcheting occurs.

The amount of preloading of the detent pins can be varied by changing the thickness of the heads of the detent pins 162—162 or 176—176 to increase the installed deflection of the disc springs 164, and 183, respectively. The sealing arrangement for this embodiment is identical to that of the first embodiment, and will not be discussed again in the interest of avoiding repetition.

As should now be evident, the apparatus of the present invention provides a braking system for the endoscope that is insensitive to fluids, such as cleaning fluids or the like, to which this type of instrument is exposed. It should be further noted that, because of the arrangement of the present control and braking system, it can be securely mounted upon the control housing of the insertion tube of an endoscope employing a minimum number of seals. The overall construction of the control and braking system is thus greatly simplified without sacrificing reliability or efficiency of operation.

While this invention has been described in detail with reference to certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention, as defined in the following claims.

What is claimed is:

1. A steering mechanism for a flexible insertion tube of an endoscope having an articulation section at its distal end and deflection cable means extending from the distal end to the proximal end thereof, said steering mechanism comprising:

a control housing operatively connected to the proximal end of said insertion tube;

a control wheel mounted for rotation on the exterior of said control housing;

connecting means for coupling said control wheel to said deflection cable means for articulating the distal end of said insertion tube;

a brake means mounted adjacent to said control wheel;

coacting means movably mounted on said control wheel for engaging said brake means to resist rotation of said control wheel; and actuating means for moving said brake means between a first position wherein said brake means is out of engagement with said coacting means and a second position wherein said brake means is in braking engagement with said coacting means.

2. The steering mechanism according to claim 1 wherein said connecting means comprises a shaft and said first position is displaced from said second position in an axial direction of said shaft.

3. The steering mechanism according to claim 2 further comprising a first biasing means for urging said coacting means toward said brake means.

4. The steering mechanism according to claim 3 wherein said coacting means comprises at least one detent pin being slidably mounted in a hole bored through said control wheel.

5. The steering mechanism according to claim 4 wherein said at least one pin has a head in contact with said biasing means for preloading of the pin.

6. The steering mechanism according to claim 5 wherein said brake means comprises a brake disc having a plurality of circumferentially arranged depressions that are serially engaged by all said detent pins when said actuating means is in said second position and said control wheel is rotated.

7. The steering mechanism according to claim 3 further comprising a second biasing means for urging said brake means away from said coacting means when said actuating means is in said first position.

8. The steering mechanism according to claim 2 further comprising a first stop means acting on said brake means for limiting movement of said brake means towards said coacting means when said actuating means is in said second position.

9. The steering mechanism according to claim 8 further comprising a second stop means acting on said brake means for limiting an excursion of said actuation means between said first position and said second position.

10. In an endoscope that has an articulation section at its distal end and first and second deflection cable means extending from the distal end to the proximal end thereof, a steering mechanism comprising:

a control housing connected to said insertion tube at the proximal end thereof;

first and second control wheels mounted for rotation upon the exterior of said housing;

connecting means comprising first means for coupling said first control wheel to said first deflection cable means for moving said distal end of the insertion tube in a vertical plane and second means for coupling said second control wheel to said second deflection cable means for moving said distal end of the insertion tube in a horizontal plane;

brake means mounted in proximity to respective control wheels, said brake means being movable axially toward and away from respective control wheels;

actuating means for moving each of said brake means between a first position wherein said brake means is disengaged from the respective control wheel and a second position wherein said brake means is in braking engagement with the respective control wheel;

a plurality of detent pins slidably mounted in holes bored through said control wheels; and first biasing means operating on each of said control wheels and acting on said pins to urge said pins in the direction of the respective brake means.

11. The steering mechanism according to claim 10 wherein said brake means are mounted on said connecting means concentric with an axis thereof.

12. The steering mechanism according to claim 11 wherein each of said brake means has formed therein a series of depressions that sequentially receive ends of said detent pins when the respective control wheel is incrementally rotated and the respective actuating means is in said second position.

13. The steering mechanism according to claim 11 that further includes a second biasing means acting on each of said brake means for urging the respective brake means out of engagement with the respective control wheel when its respective actuating means is in said first position.

14. The steering mechanism according to claim 11 wherein said connecting means comprises a shaft means secured to each control wheel for rotation therewith.

15. The steering mechanism according to claim 14 wherein said shaft means comprises an inner shaft and an outer shaft surrounding said inner shaft.

16. The steering mechanism according to claim 15 further comprising a first cylindrical support means encircling a portion of said outer shaft and a second support means passing axially through said inner shaft, said first and second support means being secured to said control housing.

17. The steering mechanism according to claim 16 further comprising first and second shaft sealing means acting respectively between said first support means and said outer shaft and between said second support means and said inner shaft, and a support sealing means acting between said first support means and the control housing.

18. The steering mechanism according to claim 16 further comprising a third shaft sealing means acting between said outer shaft and said inner shaft.

19. The steering mechanism according to claim 18 wherein said second support means extends axially beyond an outer end of the inner shaft to provide an end section for supporting the respective brake means.

20. The steering mechanism according to claim 19 wherein each support means has a square cross-sectional section for slidably supporting the respective brake means.

21. The steering mechanism according to claim 19 wherein each support means has a threaded section and the respective actuating means is threaded thereupon whereby turning the actuating means will move the brake means into and out of engagement with the detent pins of the respective control wheel.

22. The steering mechanism according to claim 20 wherein each of said actuating means further comprises a stop means for stopping said actuating means in said first position and said second position.

23. The steering mechanism according to claim 22 wherein each of said actuating means further includes a detent means for holding said actuating means in a selected one of said first position and said second position whereby an operator can detect braking disengagement and engagement in said first and second positions respectively.

* * * * *